(12) United States Patent
Brawley

(10) Patent No.: US 12,016,575 B1
(45) Date of Patent: Jun. 25, 2024

(54) EXTENDABLE RASP DEVICE AND METHOD OF MAKING THE SAME

(71) Applicant: Craig Cameron Brawley, Chicago, IL (US)

(72) Inventor: Craig Cameron Brawley, Chicago, IL (US)

( * ) Notice: Subject to any disclaimer, the term of this patent is extended or adjusted under 35 U.S.C. 154(b) by 561 days.

(21) Appl. No.: 17/221,832

(22) Filed: Apr. 4, 2021

Related U.S. Application Data

(60) Provisional application No. 63/084,538, filed on Sep. 28, 2020.

(51) Int. Cl.
*A61B 17/16* (2006.01)
*A61B 17/00* (2006.01)

(52) U.S. Cl.
CPC ...... *A61B 17/1659* (2013.01); *A61B 17/1633* (2013.01); *A61B 2017/00477* (2013.01)

(58) Field of Classification Search
CPC ...... A61B 17/1659; A61B 2017/32113; B26B 1/08
See application file for complete search history.

(56) References Cited

U.S. PATENT DOCUMENTS

| 5,342,365 | A  | * | 8/1994  | Waldman         | A61B 17/1659 |
|           |    |   |         |                 | 407/29.1     |
| 8,048,080 | B2 |   | 11/2011 | Bleich et al.   |              |
| 8,617,164 | B2 |   | 12/2013 | Nelson et al.   |              |
| 2012/0232658 | A1 | * | 9/2012 | Morgenstern Lopez | A61F 2/447 |
|           |    |   |         |                 | 606/90       |

FOREIGN PATENT DOCUMENTS

EP     2 708 194 B1    5/2015

* cited by examiner

*Primary Examiner* — Andrew Yang
(74) *Attorney, Agent, or Firm* — Jayne M. Saydah

(57) ABSTRACT

A bone rasp device with a protective sheath and an extendable and retractable rasp for protection of the skin and soft tissue from the rasp during insertion and removal of the tool. The rasp device includes a tubular body having an interior surface defining a central opening extending between a first end and a second end with the first end defining a first aperture. A rasp portion, including a rough surface opposite a smooth surface, is connected to the tubular body and positioned within the central opening of the tubular body. The rasp portion is moveable relative to the tubular body. In a first position, the rough surface is contained within the central opening, and in a second position, with the rasp portion extends through the first aperture such that the rough surface is positioned outside the central opening and tubular body.

19 Claims, 10 Drawing Sheets

FIG. 11A
FIG. 11B
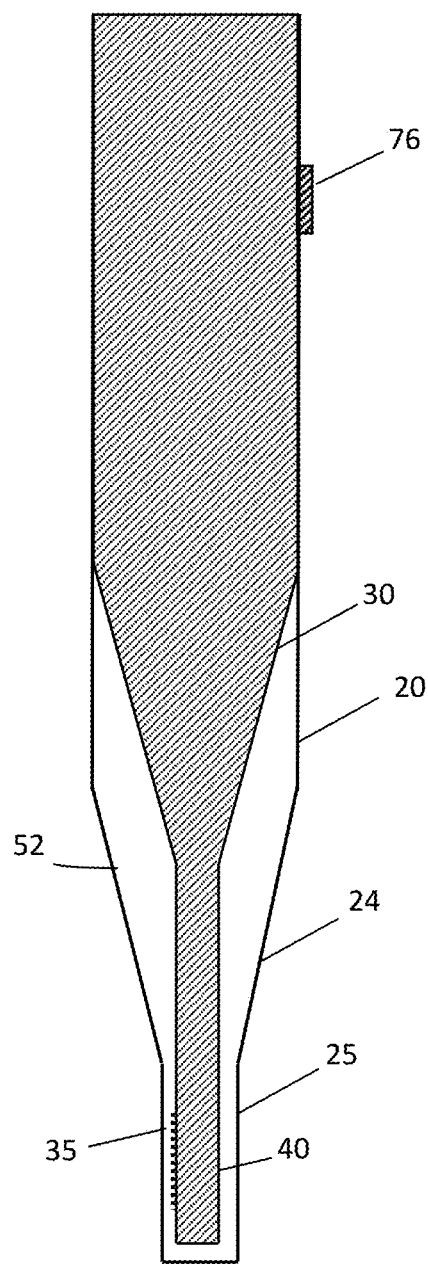
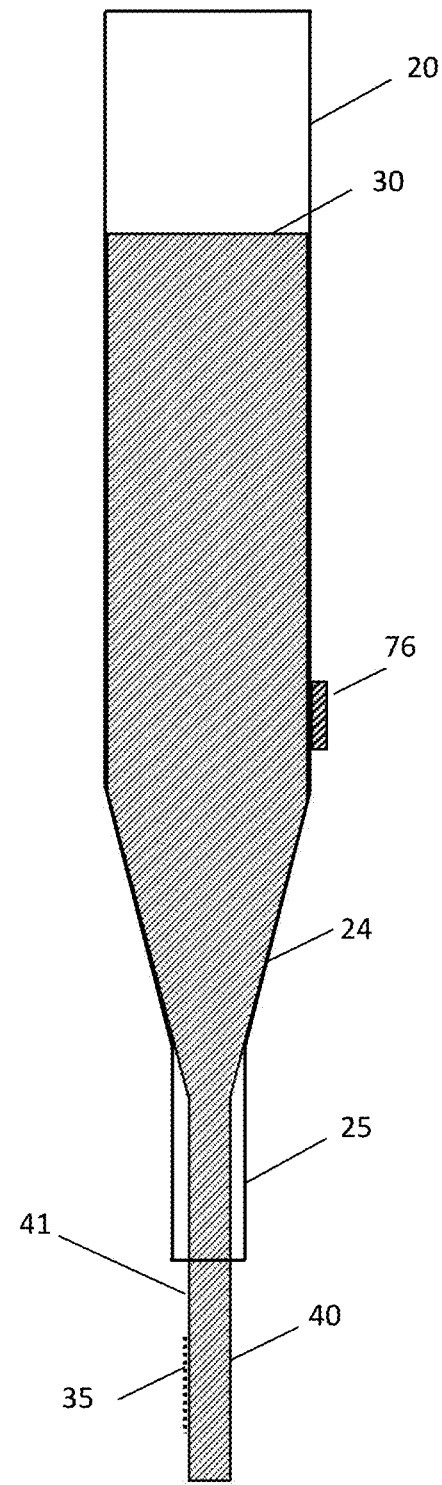

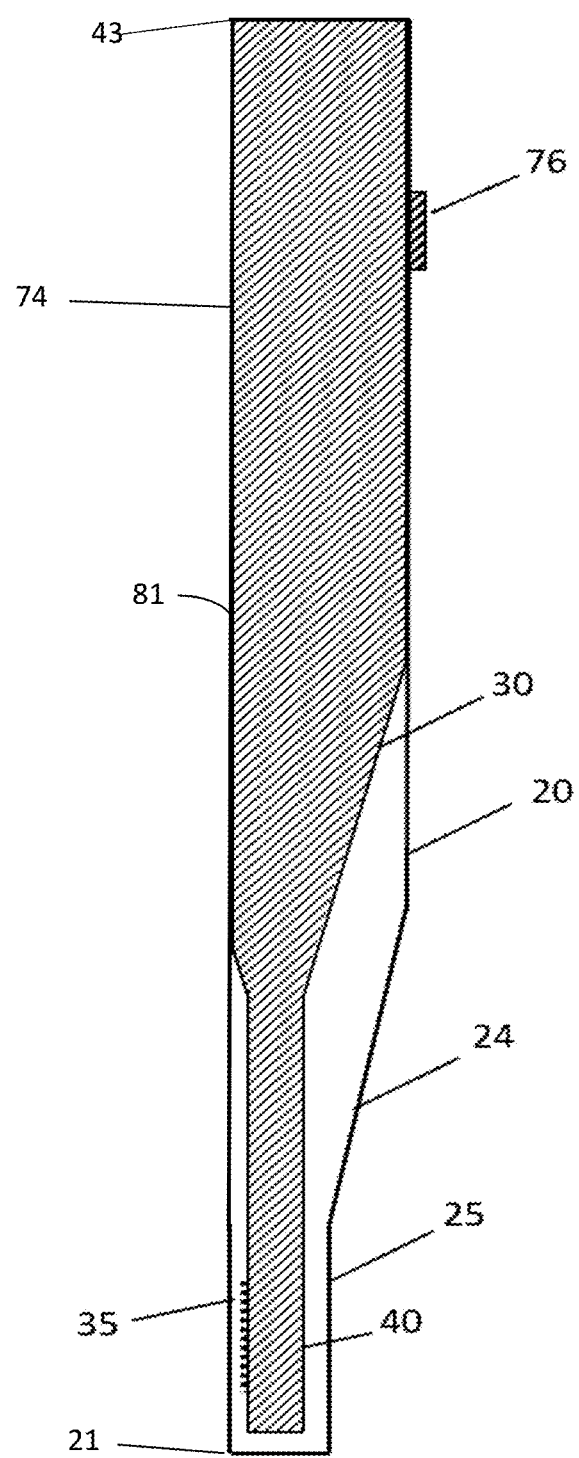

EXTENDABLE RASP DEVICE AND METHOD OF MAKING THE SAME

CROSS-REFERENCE

This application claims the benefit of priority from U.S. Provisional Application No. 63/084,538 filed Sep. 28, 2020, the contents of which are herein incorporated by reference in their entirety.

BACKGROUND OF THE INVENTION

1. Field of the Invention

The present invention relates generally to a bone rasp surgical tool for removing and contouring bone. More specifically, the invention relates to a bone rasp including a protective sheath over a retractable rasp.

2. Description of the Related Art

Bone rasps are a surgical tool used for bone filing, contouring and/or modeling. Conventional surgical rasp tools have a grip area from which the rasp portion extends. One side of the tool has a rough (eg. serrated, coarse, and/or knurled) surface, while the other side of the tool, opposite the rough side, may be a smooth surface. Bone may be contoured or removed with the rasp, by moving (eg. rubbing, grating, and/or filing) the rough surface across undesirable bone formations until the desired contour is achieved.

To contour bone with a bone rasp, the bone rasp is advanced subcutaneously or submucosally to the location on a bone until the rough surface is able to contact the bone that is in need of contouring. This advancement maybe through a soft tissue and/or an orifice such as a nostril, ear canal, oral cavity and eye socket. Once the rasp is in position, pressure may be applied to the smooth surface as the rough surface is moved across the bone. For example, the bone rasp may be moved back and forth across the bone with generally horizontal force applied to the grip while generally vertical force is also applied to the skin directly over the smooth surface.

Upon entering the orifice and/or the surgical opening, the rough surface of the rasp may contact soft tissues, such as the skin, blood vessels, muscles, and/or nerves. As the rasp is advanced to the bone contour site, it is important to ensure the rasp moves smoothly across the soft tissues, therefore an improvement to the bone rasp surgical tool is desired.

BRIEF SUMMARY OF THE INVENTION

The following is intended to be a brief summary of the invention and is not intended to limit the scope of the invention.

The extendable bone rasp is a rasp with a protective sheath. The sheath protects the skin and other structures under the skin from the rasp until the bone is reached. Once the bone is reached, the rasp is advanced past the sheath to remove and contour the bone.

A preferred embodiment, according to this disclosure, of the surgical rasp device comprises a tubular body having an interior surface defining a central opening extending between a first body end and a second body end, and the first body end defining a first aperture. The surgical rasp device also comprises a rasp portion connected to the tubular body and positioned in the central opening of the tubular body. The rasp portion also includes a first side with a rough surface configured to contour bone, and the rasp portion is moveable, relative to the tubular body, within the central opening. Additionally, the rasp portion includes a first position with the rough surface contained within the central opening and a second position with the rasp portion extending through the first aperture such that the rough surface is positioned external to the tubular body, and the rasp portion is moveable from the first position to the second position.

The rasp portion of the surgical rasp device may further comprise a substantially smooth surface opposite and parallel to the rough surface.

The surgical rasp device may further comprise a first locking mechanism on the tubular body, and a second locking mechanism connected to the rasp portion and interlocking with the first locking mechanism. The first and second locking mechanisms may connect the tubular body to the rasp portion and allow the rasp portion to move relative to the tubular body from the first position to the second position.

The surgical rasp device may further comprise a central body connected to the surgical rasp portion. The central body is positioned in the central opening and within the tubular body, and the central body includes an outer surface extending around the perimeter of the central body with the outer surface facing the interior surface of the tubular body. Also, a pin is connected to the central body, and the pin extends from the annular surface of the central body towards the tubular body.

The tubular body may further comprise a slot extending through an outer surface of the tubular body, and the pin extending from the central body through the slot. Additionally, the tubular body may further include a centerline extending in a longitudinal direction, and the slot extends in the longitudinal direction with respect to the center line.

The slot may further comprise a first slot end configured to hold the pin when the rasp portion is in the first position, and a second slot end configured to hold the pin when the rasp is in the second position.

In another aspect of this embodiment, the tubular body includes a centerline extending in a longitudinal direction. Also, the slot further comprises a first segment extending in the longitudinal direction, and a second segment extending substantially transverse to the centerline.

In yet another aspect of this embodiment, the tubular body further comprises a first body section including a first interior surface, and the rasp portion further comprises a central body connected in-line with the rasp portion. Also, the central body is located in the central opening of the tubular body, and the annular central body circumferentially abuts the first annular interior surface.

The tubular body may further comprise a tubular rasp cover portion at the first body end; the tubular rasp cover portion includes the aperture at one end; and the tubular rasp cover portion extending in a longitudinal direction. Also, a tubular abutment cover portion connects to the rasp cover portion; the abutment cover portion directly connects to a second end of the rasp cover portion; and the abutment cover portion extends in a transverse direction relative to the rasp cover portion. Also, a handle cover portion connects directly to the abutment cover portion, and the handle cover portion extends in the longitudinal direction from the abutment cover portion toward the second body end. Additionally, the central opening extends through the rasp cover portion, abutment cover portion and handle cover portion.

The surgical rasp device may also further comprise a central body extending between a first central end and a second central end, and the rasp portion positioned at the first central end with the rasp portion extending in a longitudinal direction from the first central end towards the second central end. Additionally, the surgical rasp device further comprises a central body abutment portion connected directly to the rasp portion, and the central body abutment portion extends in a transverse direction relative to the rasp portion. Also, the surgical rasp device comprises a handle portion directly connected to the central body abutment portion, and the handle portion extends in the longitudinal direction from the central body abutment to the second body end.

In yet another aspect, the surgical rasp device includes, in the first position, the cover abutment portion directly contacting the central body abutment portion, and in the second position, the cover abutment portion and the central body abutment portion spaced apart.

Another embodiment of the present invention, according to this disclosure is a rasp device comprising a tubular body having an interior surface defining a central opening extending between a first body end and a second body end with the first body end defining an aperture. The rasp device also comprises a rasp portion connected to the tubular body and positioned in the central opening of the tubular body. The rasp portion includes a first side with a rough surface, and the rasp portion is moveable, relative to the tubular body, within the central opening. Additionally, the rasp portion has a first position with at least the rough surface contained within the central opening, and a second position with the rasp portion extending through the aperture such that the rough surface is positioned external to the tubular body, and the rasp portion is moveable from the first position to the second position.

The rasp portion may further comprise a second side opposite and parallel to the first side, and the second side includes a substantially smooth surface opposite and parallel to the rough surface.

In another aspect, the rasp device further comprises a first locking mechanism on the tubular body, and a second locking mechanism connected to the rasp portion and interlocking with the first locking mechanism. Also, the first and second locking mechanisms connect the tubular body to the rasp portion and allow the rasp to move relative to the tubular body from the first position to the second position.

The tubular body further comprises a tubular rasp cover portion at the first body end. Also, the tubular rasp cover portion includes the aperture at one end, and the tubular rasp cover portion extends in a longitudinal direction. The tubular body also further comprises a tubular abutment cover portion connected to the rasp cover portion, the abutment cover portion directly connected to a second end of the rasp cover portion, and the abutment cover portion extending a transverse direction relative to the rasp cover portion. Additionally, the tubular body further comprises a handle cover portion connected directly to the abutment cover portion, and the handle cover portion extending in the longitudinal direction from the abutment cover portion to the second body end. Also, the central opening extends through the rasp cover portion, abutment cover portion, and handle cover portion.

In another aspect of this embodiment, the rasp device further comprises a central body extending between a first central end and a second central end. Also, the rasp portion is positioned at the first central end, and the rasp portion extends in a longitudinal direction from the first central end towards the second central end. Additionally, the rasp device comprises a central body abutment portion connected directly to the rasp portion, and the central body abutment portion extends in a transverse direction relative to the rasp portion. Also, a handle portion directly connects to the central body abutment portion, and the handle portion extends in the longitudinal direction from the central body abutment portion to the second body end.

In another aspect, the tubular body may comprise a first length extending between the first body end and the second body end. Also, the rasp portion further comprises a first rasp end adjacent the rough surface; a second rasp end entirely within the tubular body; and a second length extending between the first rasp end and the second rasp end, the second length being less than the first length.

A third embodiment of the invention, according to this disclosure, is, a method of making a rasp device. The method comprising the following steps. A tubular body is provided and the tubular body includes a sidewall extending in a longitudinal direction between the first body end and the second body end, a first length between the first and second body ends, an interior surface on the sidewall defining a central opening, the interior annular surface and central opening extending between the first body end and the second body end, a slot extending through the sidewall, the slot extending relatively further in the longitudinal direction than the transverse direction, and an aperture at the first body end, and an opening at the second body end. In another step, a central body is provided wherein the central body extends in the longitudinal direction between a first body end, a second body end, and the central body includes a second length extending between the first body end and the second body end, the second length being less than the first length. The central body also includes a rasp portion formed at the first body end, and the rasp portion includes a first side opposite and parallel to a second side and the first side including a rough surface and the second side being entirely smooth. Additionally, the central body includes a handle portion connected to the rasp portion and the handle portion extending longitudinally between the rasp portion and the second body end. An additional step includes placing a hole in the handle portion of the central body and the hole is positioned on the handle portion such that the hole is located within the slot when central body is inserted in the tubular body. Other steps include inserting the central body into the opening in the second body end of tubular body until the central body is contained within the tubular body and the hole is positioned within the slot and inserting a pin into the hole in the handle portion of the central body.

The step of providing the central body further comprises the step of providing a central body abutment portion between the rasp portion and the handle portion, the central body abutment portion directly connected to the rasp portion and directly connected to the handle portion, and the central body abutment extending in a transverse direction.

The step of providing the tubular body further comprises the steps of providing a tubular rasp cover portion at the first tubular end, and the tubular rasp cover portion including the aperture at one end; providing a tubular abutment cover portion connected to the rasp portion, and the abutment cover portion directly connected to a second end of the rasp cover portion; and providing a handle cover portion connected directly to the abutment cover portion, and the handle cover portion extending longitudinally from the abutment cover portion to the second body end. Also, the central opening extends through the rasp cover portion, abutment cover portion and handle cover portion.

BRIEF DESCRIPTION OF THE SEVERAL VIEWS OF THE DRAWINGS

The foregoing summary, as well as the detailed description of the preferred embodiments of the present invention, will be better understood when read in conjunction with the appended drawings. For the purpose of illustrating the invention, there is shown in the drawings, which are diagrammatic, embodiments that are presently preferred. It should be understood, however, that the present invention is not limited to the precise arrangements and instrumentalities shown. In the drawings:

FIG. 11A is a cross sectional, side view along the center line of FIG. 10B and depicts the position of the central body of the surgical rasp, with respect to the outer cover, in the retracted position;

FIG. 11B is a cross sectional, side view along the center line of FIG. 10B and depicts the position of the central body of the surgical rasp, with respect to the outer cover, in the extended position;

FIG. 12 depicts another embodiment of the surgical rasp tool of this invention having a substantially linear underside;

DETAILED DESCRIPTION OF THE INVENTION

Certain terminology is used in the following description for convenience only and is not limiting. The words "inner", "inwardly" and "outer", "outwardly" refer to directions toward and away from, respectively, a designated centerline or a geometric center of an element being described, the particular meaning being readily apparent from the context of the description. Also, as used herein, the words "connected" or "coupled" are each intended to include integrally formed members, direct connections between two distinct members without any other members interposed therebetween and indirect connections between members in which one or more other members are interposed therebetween. The terminology includes the words specifically mentioned above, derivatives thereof, and words of similar import.

Figure 6:
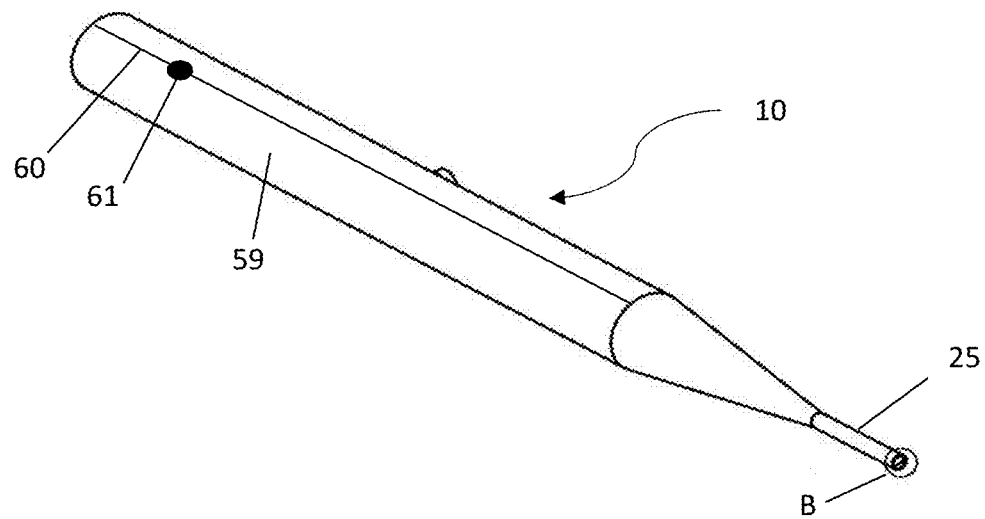
FIG. 6 depicts the of the bone rasp tool of FIG. 1A in the retracted position.
Figure 7:
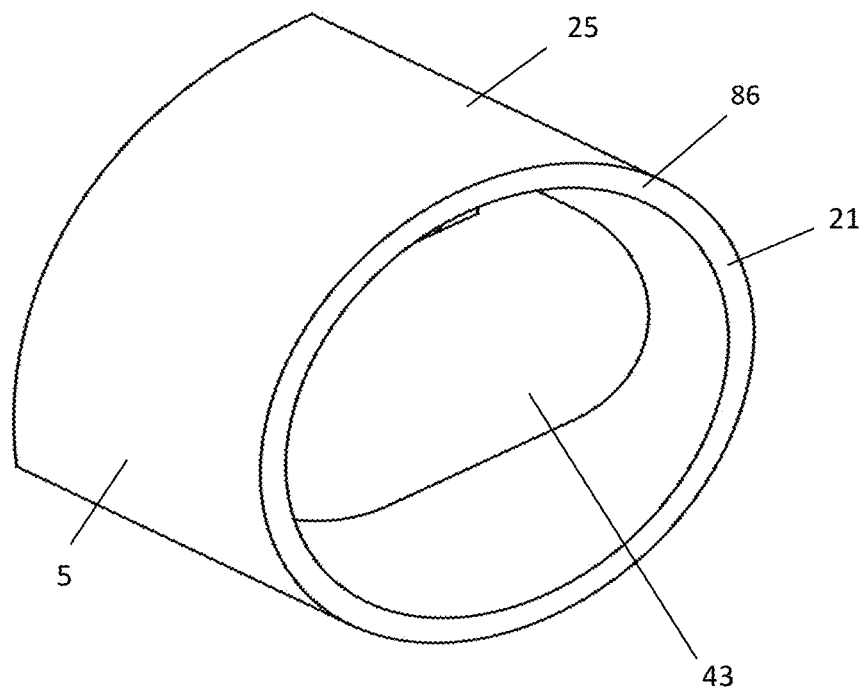
FIG. 7 is an exploded view of area B showing the rasp tool retracted and enclosed in a sheath.
Figure 8:
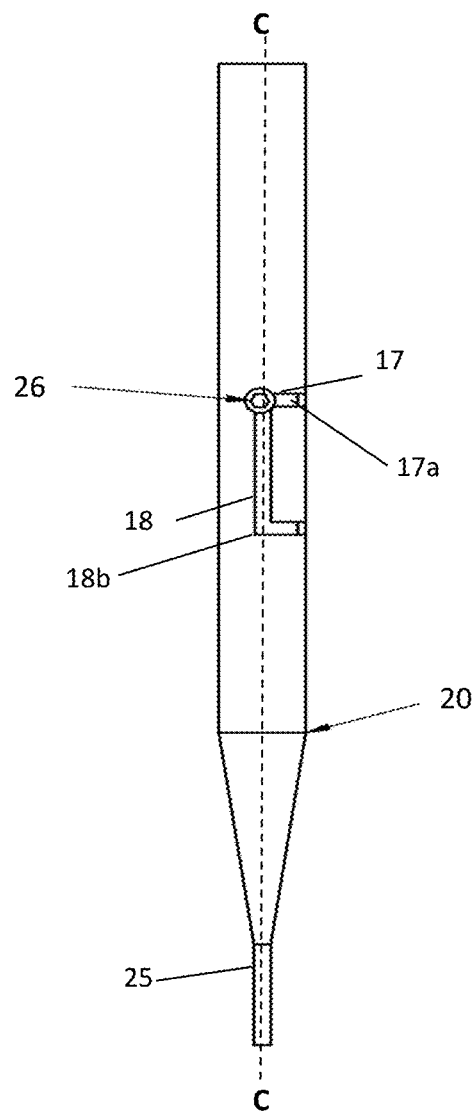
FIG. 8 depicts the embodiment of the invention in FIG. 1 with a u-shaped slot mechanism for moving and securing the rasp portion in a retracted position.
Figure 9:
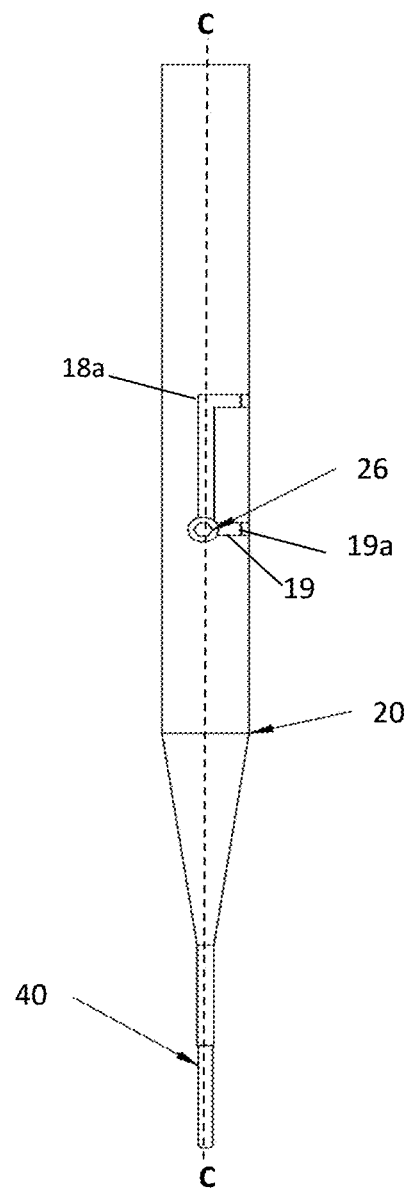
FIG. 9 depicts the embodiment of the invention in FIG. 1 with the u-shaped slot mechanism for moving and securing the rasp in an extended position

Referring now to the drawings in detail, wherein like numbers are used to indicate like elements throughout, there is shown in FIG. 1A-1B and FIGS. 2-9, a preferred embodiment of a rasp tool 10 including an outer cover 20, central body 30 including a rasp portion 40 extending from inside the outer cover 20 and a movement locking mechanism 50. The rasp portion 40 includes a rough surface 35 and may retract into the outer cover 20 and extend from the outer cover 20, as shown in FIGS. 8 and 9, respectively. The rasp tool 10 is designed for bone contouring and is suitable for rhinoplasty and other forms of surgery that involve bone contouring. Additionally, the rasp tool 10 may be used in other fields such as manicures/pedicures, pottery, woodworking, etc.

The outer cover 20 serves as a protective sheath and a barrier between the body and rough surface 35 of the surgical rasp portion 40. This allows the surgical rasp tool 10 to be used for bone filing and contouring and provides protection to soft tissues such as skin, blood vessels, muscles, and/or nerves. More specifically, rasp portion 40 may remain contained in the outer cover 20 as the tool 10 is advanced through a bodily orifice and/or surgical opening in the tissue. Once the tool is advanced to the desired position near the bone formation to be contoured, the rasp portion 40 may be extended and rasping may begin. After the bone formation is contoured, the rasp portion 40 may be retracted into the outer cover 20, and then, the tool 10 may be removed from the surgical opening or the tool 10 may be repositioned at another bone formation to be filed or contoured. Covering the rough surface 35 as the rasp tool 10 is moved through the body reduces the risk of any soft tissue injuries or damage resulting from contact with an uncovered rasp.

The central body 30 may be formed around a central axis or centerline C and includes a handle portion 31, conical section 34, and a locking or securing pin 26 extending outwardly, as well as a conical portion 34 and a rasp portion 40. The rasp portion 40, abutment portion 34, and handle portion 31 are connected such that the portions 31, 40 and 34 are in-line and extend in the longitudinal direction along the centerline C. The handle portion 31 is elongated and cylindrical and has an outer annular or circular surface 32 extending between a handle end 33 and the conical section 34.

The abutment portion 34 in this embodiment may be conical and include a base 36 and an apex 3. The base 36 has a relative larger diameter than the apex 3. The base 36 may be contiguous with the annular surface 32 and handle portion 31. Also, the abutment portion 34 has an outer conical surface 9. The rasp portion 40 extends from the apex 3 of the conical section 34 in a direction opposite and/or away from the handle end 33.

Figure 3:
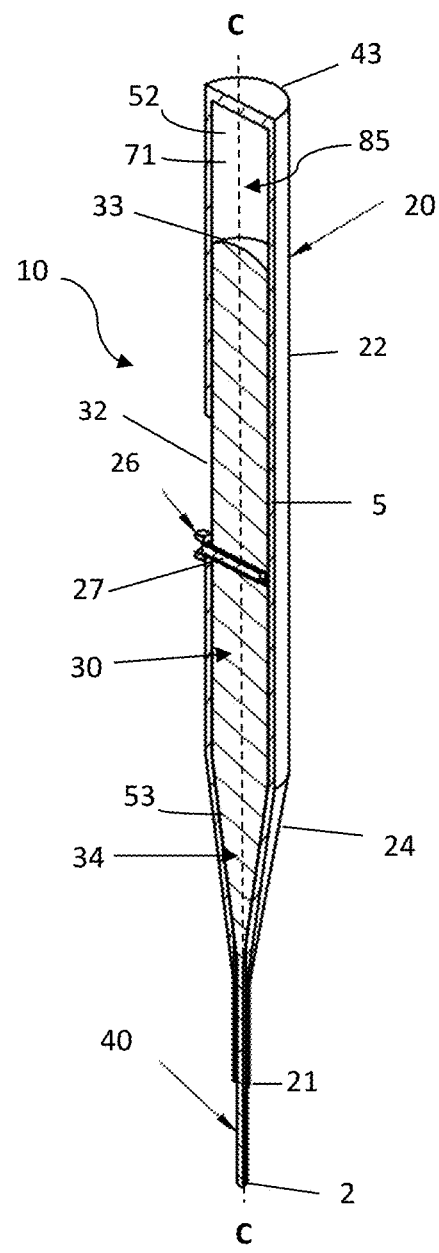
FIG. 3 is a cross sectional view of the bone rasp tool of FIG. 2 along line A-A.

Due to its conical shape, the abutment portion 34 extends in both the longitudinal and transverse directions. Additionally, as shown in FIGS. 1A and 3, the abutment portion 34 is a right cone with the apex 3 centered over the base 36. This allows the abutment portion 34 to extend uniformly in the longitudinal and transverse directions and to be symmetrical about the centerline C.

The locking or securing pin 26 is a threaded fastener such as a screw and may be rotationally inserted into a threaded receiving hole 27 formed in the side of the outer annular surface 32 of the handle portion 31. Other locking mechanisms are envisioned. For example, the fastener may be formed integral with the handle portion 31 and/or it may be a pin rather than a threaded fastener, etc. Additionally, pin 26, as shown, has an elongated threaded portion 87 extending from a relatively wider, second portion 89. It is envisioned that pin 26 may also be formed and used without the relatively wider, second portion 89.

In the preferred embodiment, the central body 30 and locking pin 26 may be formed of surgical steel, but it is envisioned that other suitable materials such as other metallic materials/alloys, ceramic, and plastics maybe used. Additionally, the central body 30 may be formed as one piece with the handle portion 31, conical section and rasp portion 40 integrally formed. The central body 30 may be produced using various techniques known in the art. For example, metallic, ceramic, and plastic materials may be molded, cast and/or produced via additive manufacturing. Another example is milling metallic compounds such as with a computer numerical control (CNC) machine. Additionally, any pieces that are formed separately may be welded together or affixed with other suitable methods.

It is also envisioned that the central body 30 may be formed with the different sections made from different types of materials. For example, the handle portion 30 and the rasp portion 40 may be formed of two different types of surgical steel with the rasp portion 40 having a greater strength than the handle portion 31. Additionally, the handle portion 31 and rasp portion 40 may be formed separately and connected such that the base of the rasp portion 40 rotates into the handle portion 31 and is secured by a threaded fastening system. This has the benefit of allowing for replacing the rasp portion 40 to select a different type of rasp surface or size and allows replacement for wear.

Figure 1B:
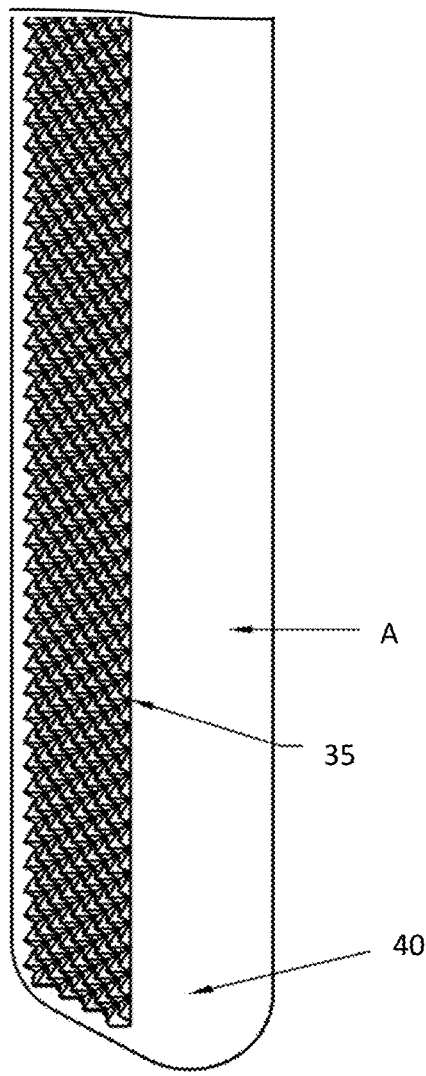
FIG. 1B is an exploded view of area A of FIG. 1A and depicts the rough surface of the bone rasp tool.
Figure 1A:
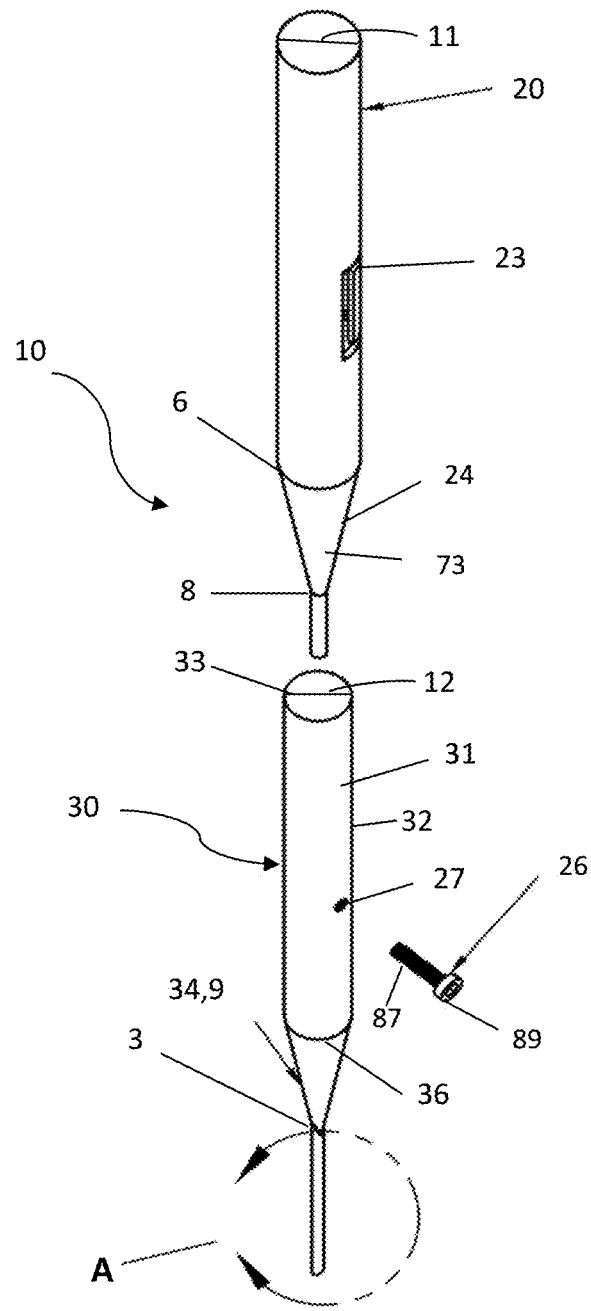
FIG. 1A is an expanded view of a preferred embodiment of the bone rasp tool according to this invention.
Figure 2:
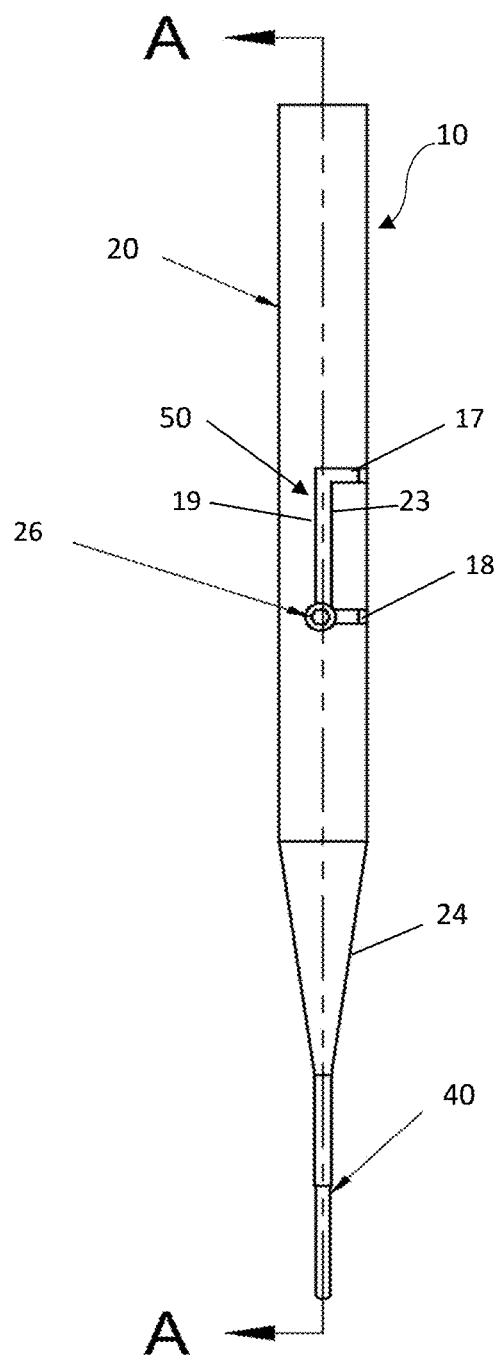
FIG. 2 is a side view of the bone rasp tool of FIG. 1A with the rasp portion exposed.
Figure 4:
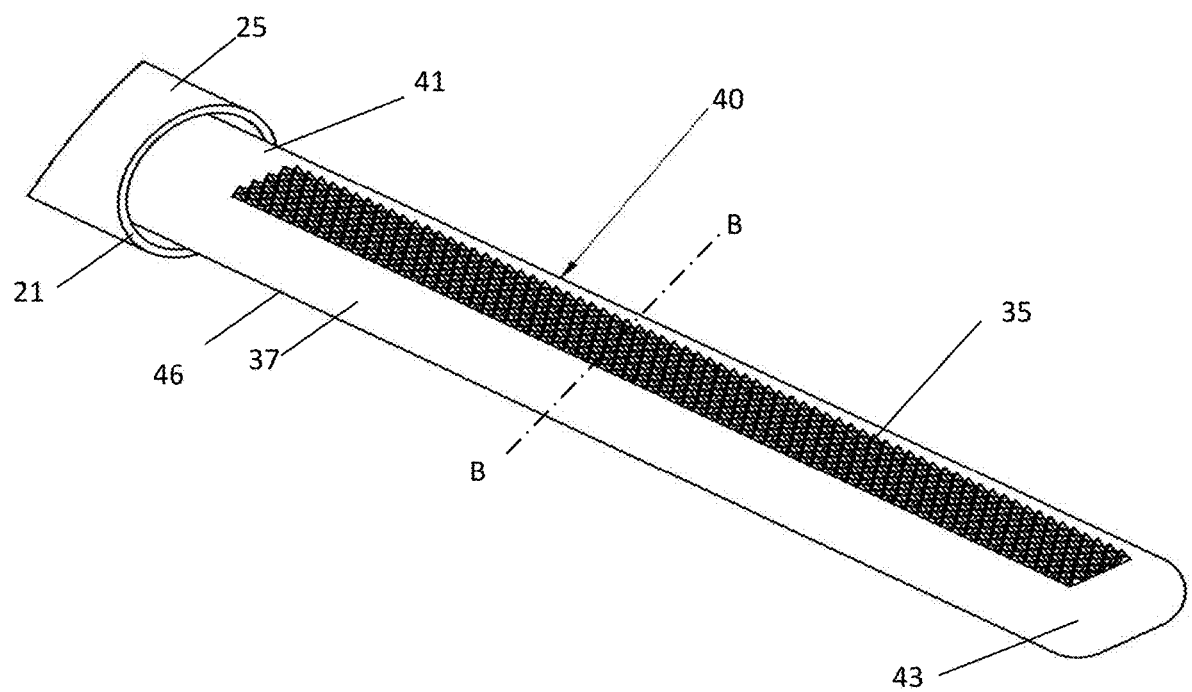
FIG. 4 depicts the bone rasp tool of FIG. 1A with the rasp extended position.
Figure 5:
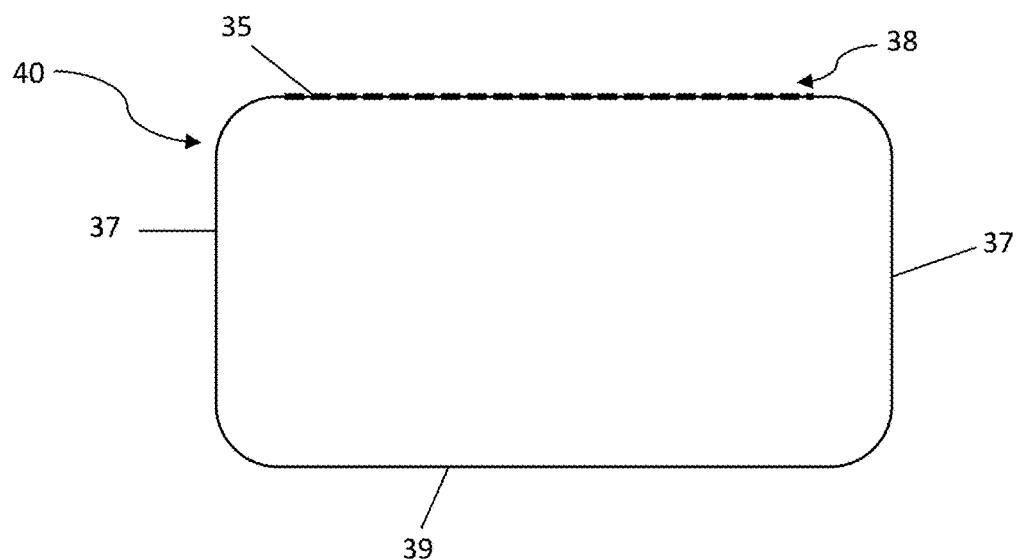
FIG. 5 is a cross sectional view of the bone rasp tool along line B-B of FIG. 1A and depicts a cross section including the rough surface.

As shown in FIGS. 1B, 4, and 5, the rasp portion 40 includes an outer surface 46 with a rough surface section 35 opposite and a relatively less rough or smooth surface 39. Rough and smooth surfaces 35 and 39, respectively, are connect via rounded side surfaces 37, which are also smooth and relatively less rough than surface 35. The rough surface 35 and smooth surface 39 may be substantially parallel to one another, as shown in FIG. 5, which depicts a cross section, along line B-B of FIG. 4. Additionally, the rough surface 35 may be formed such that the roughness extends from an essentially linear or planar surface, as shown in FIG. 5, or the roughness may extend from a curved surface, as may be necessary or allowable for different applications.

As known in the art, the rough surface 35 may be made of the same material as the rasp portion 40 and formed by methods known in the art such as milling or CNC machining. Additionally, as known in the art, the rough surface 35 may be of different materials than rasp portion 40 so rough surface 35 may be relatively harder than the rasp portion 40. For example, the rasp may have a diamond surface while the remainder of the rasp portion 40 comprises surgical steel.

The rough surface 35 may be formed with various characteristics. The type of rough surface 35 may be serrated, toothed, ridged, notched and/or knurled, etc. Also, the degree of roughness may be relatively fine or coarse and the rough surface 35 may have varying degrees of roughness in different areas of surface 35.

FIGS. 1B, 4 and 5, depict the rough surface 35 being limited to an area of the outer surface 46 such that the surface portion 41 between the abutment section 34 and rough surface section 39 is smooth. Additionally, the rough surface section 35 extends across a substantially planar surface portion 38 of outer surface 46. However, in other embodiments, the dimensions of the rough surface section 39 may vary. For example, the length of the rough surface section 39 may extend from the conical section 34 to the opposite end 43 of the rasp portion 40. Also, the rough surface section 39 may extend laterally across the entire planar surface portion 38 or have a width less than the planar surface. Further, the rough surface 35 may also extend across a non-planar surface if desired.

The outer cover 20 includes a side wall 5 which, in the present embodiment, forms a tubular body having an annular or circular cross section. The wall 5 extends between an end aperture 21 and end surface 43, which may be closed. Between the aperture 21 and end surface 43, the wall 5 forms three substantially annular and tubular portions 22, 24 and 25. The wall 5 has an interior annular surface 71 that defines a central opening 85 that extends from the aperture 21 to the end surface 43.

The three substantially tubular and annular sections formed by the side wall 5 include a handle cover portion 22, an abutment cover portion 24 and a rasp cover portion 25. Each of the three portions 22, 24 and 25 are connected, such that each portion 22, 24, 25 are coaxial and in-line. The abutment cover portion 24 in this embodiment has a conical shape and has an apex 8 and a base 6, and cover portion 24 extends between the handle cover portion 22 and the rasp cover portion 25. Additionally, the abutment cover portion 24 has an annular and conical interior surface 53.

Due to its conical shape, the abutment cover portion 24 extends in both the longitudinal and transverse directions. Additionally, as shown in FIGS. 1A and 3, the abutment cover portion 24 is a right cone with the apex 8 centered over the base 6. This allows the abutment portion 24 to extend uniformly in the longitudinal and transverse directions and to be symmetrical about the centerline C.

The rasp cover portion 25 extends between the aperture 21 and abutment cover portion 24. At one end of the rasp cover portion 24 the wall 5 defines the aperture 21 and the other end of the rasp cover portion 24 is directly connected to the apex 8 or narrower end of the cover portion 24. The handle cover portion 22 is cylindrical and connected to and abuts portion 24 such that the handle cover portion 22 is directly connected to the relatively widest cross section or base 6 of the abutment cover portion 24. Both the rasp cover portion 25 and handle cover portion 22 extend longitudinally between the first end 21 of the outer cover and the second end 43 of the outer cover.

Each of portions 22, 24 and 35 are tubular and the central opening 85 extends within each portion 22, 24 and 35. Within the abutment cover portion 24, the interior surface 71 defines the conical interior surface 53. Within the rasp cover portion 22 and handle cover portion 25, the interior surface 53 defines an annular or circular surface.

Additionally, the outer cover 20 includes a slot 23 which may secure or lock the central body 30 in a particular position and allows the central body 30 to rotate and move longitudinally with respect to the outer cover 20. It is noted that the end surface 43 could also be an aperture rather than a closed end.

The aperture 21 is defined by the wall 5 at the end of the rasp cover portion 24. As shown in FIG. 7, the aperture 21 may be formed with a linear or relatively straight outer surface 86, which is substantially perpendicular to the centerline C. It is noted that other configurations for surface 86 are considered. For example, surface 86 may be formed with a curved or tapered edge to create a narrower profile.

Slot 23 is a u-shaped slot or opening in the handle cover portion 22 extending entirely through the handle cover 22.

The u-shape is formed of two equal length slots 17 and 18 extending substantially in the radial direction with respect to the central axis C, and a third slot 19 contiguous with slots 17 and 18 and extending substantially in the axial or longitudinal direction or parallel to the central axis C.

The outer cover 20 of may be formed of surgical steel, but it is envisioned that other suitable materials such as other metallic materials/alloys, ceramic, and plastics maybe used. Also, the outer cover 20 may be produced using various techniques known in the art such as molding, casting and/or additive manufacturing. For example, metallic, ceramic and plastic materials may be molded or cast. Another example is milling metallic compounds such as with a CNC machine. It is important to note that the rasp cover portion 25 may be made of a separate material, such as plastic, in comparison to the other sections, which may be made of metallic materials/alloys, ceramics, etc.

Additionally, the outer body 30 may be formed as one piece with the handle cover portion 22, abutment cover portion 24, and rasp cover portion 25 integrally formed. However, it is also envisioned that each of these sections may be formed separately and connected via adhesive or mechanical fastening such as clips or threaded fastening systems.

The outer cover 20 may be of similar and complimentary shape to the central body 30 and may also formed around the centerline C such that the central body 30 and outer cover 20 are coaxial, and the central body 30 may move rotationally and longitudinally within the outer cover 20. The annular surface 32 and conical surface 38 of central body 30 abut the interior handle surface 52 and interior conical surface 53, respectively. As shown in FIG. 3, both the handle portion 31 and the handle cover 22 have diameters 11 and 12, respectively, and diameter 12 has a length relatively less than diameter 11. Further, the dimensions such as diameter and height of the conical section 34 may be relatively less than the dimensions of conical cover portion 24 such that conical surface 38 and 53 abut forming a stable connection between the outer cover 20 and central body 30.

Each of the three portions 22, 24 and 25 of the outer cover 20 have a relative greater diameter than the corresponding sections of the central body 30. More specifically, the inside diameter of the outer cover 20 is great enough to allow the central body 30 to rotate within the outer cover 20 and to allow central body 30 to translate axially along the centerline C so the rasp portion 40 may extend from the rasp cover portion 25.

The overall length is another difference between the outer cover 20 and central body 30. To fully retract into the outer cover 20, the length of the central body 30 is relatively less than the length of the outer cover 20. That is longitudinal length, extending along the centerline C, is less than the length of the outer cover 20 extending in the same direction. More specifically, the length of the central body 30 extending from the central body end surface 33 to the end 2 of the rasp portion 40 is less than the length of the outer cover extending from the end surface 43 to the aperture 21.

Other differences between the outer cover 20 and central body 30 include the lengths of the various portions/sections. The rasp portion 40 is relatively longer than the rasp cover portion 25. On the other hand, the length of the handle portion 22 is relatively less than length of the handle cover portion 31. The relatively shorter length of the handle portion 22 allows the relatively longer length of the rasp portion 40 to be fully contained within the outer body 20.

FIGS. 8 and 9 show the central body 30 translating along the central axis C, while the outer cover 20 remains stationary. This allows the rasp portion 40 to move, from a retracted or first position within the outer cover 20 through aperture 21 to the second or extended position with the rough surface 35 positioned external to the outer cover 20 and central opening 85. To release the rasp portion 40 from the retracted position of FIG. 8, the central body 30 is rotated with respect to the outer cover 20. This may be done by first securing the outer cover 20 in a stationary position. For example, the outer cover may be held by a hand or clamp. Next, the central body 30 is rotated around the central axis C by manually moving pin 26 laterally from position 17a to the junction of slots 17 and 18 at position 18a. To accomplish the longitudinal translation, pin 26 is manually moved through slot 18 from position 18a to position 18b at the junction of slots 18 and 19. Now, the rasp portion 40 will be fully extended through aperture 21. To secure or lock the extension of the rasp portion 40, the central body 20 is rotated by manually moving pin 26 laterally to position 19a. It is envisioned that pin 26 may be moved by a second hand or other mechanism such as a robotic surgery device.

Once in the second or extended position, the rough surface 35 may be moved over the bone formation for contouring. The contouring is performed with bi-manual pressure with one hand moving the rasp tool 10 and the other hand applying pressure to the skin over the smooth side of the rasp portion 40, which is under the skin. As this movement occurs, the locking mechanism as well as the direct contact between the abutment portion 34 with the abutment cover portion 24 and provide a secure connection between the outer cover 20 and central body 30 such that the central body 30 and outer cover 20 do not move relative to one another. In this case, the direct contact of the abutment portions 24 and 34 provides friction and bearing surfaces to resist movement. As a result, it is important to configure the dimensions of the central body 30 and outer cover 20 so that proper abutment occurs in the extended position.

The first or retracted position is maintained by securing the locking mechanism 50 in slot 17 at position 17a and may be maintained by the friction between the central body 30 and outer cover 20. As shown in FIGS. 11A and 11B the central body abutment portion 34 may not contact the abutment cover portion 24 in the retracted position.

As shown in FIG. 6, the exterior cover surface 59 may have a sight line 60 or mark(s) 61 formed on the surface by processes during formation as discussed above and also by etching, machining or painting, etc. These marks correspond to the orientation of the rough surface 35 of the rasp portion 40. For example, when the line 60 or mark 61 is facing up, the rough surface 35 will be oriented in the downward position towards the area to be contoured.

It is noted that other locking mechanisms 50 are envisioned for the surgical rasp tool 10 according to this invention. For example, as shown in FIGS. 10A to 10C, 11A and 11B, a linear slot system 80 is shown in the extended (FIG. 10A) and retracted (FIG. 10B) positions. The linear slot system 80 includes a button or knob 76 and a substantially longitudinal slot 70 extending parallel to the centerline C. Manual and/or mechanical force may be applied to the button or knob 76 at position 78 so that the central body 30 can move from the retracted position 78 to the extended position 77. To secure the central body 30 in either of these positions, the slot 70 may have a series of teeth or notches at positions 77 and 78 corresponding to full retraction and full extension, respectively, of the rasp portion 40 or utilize other telescoping methods.

Figures 10A, 10B, 10C:
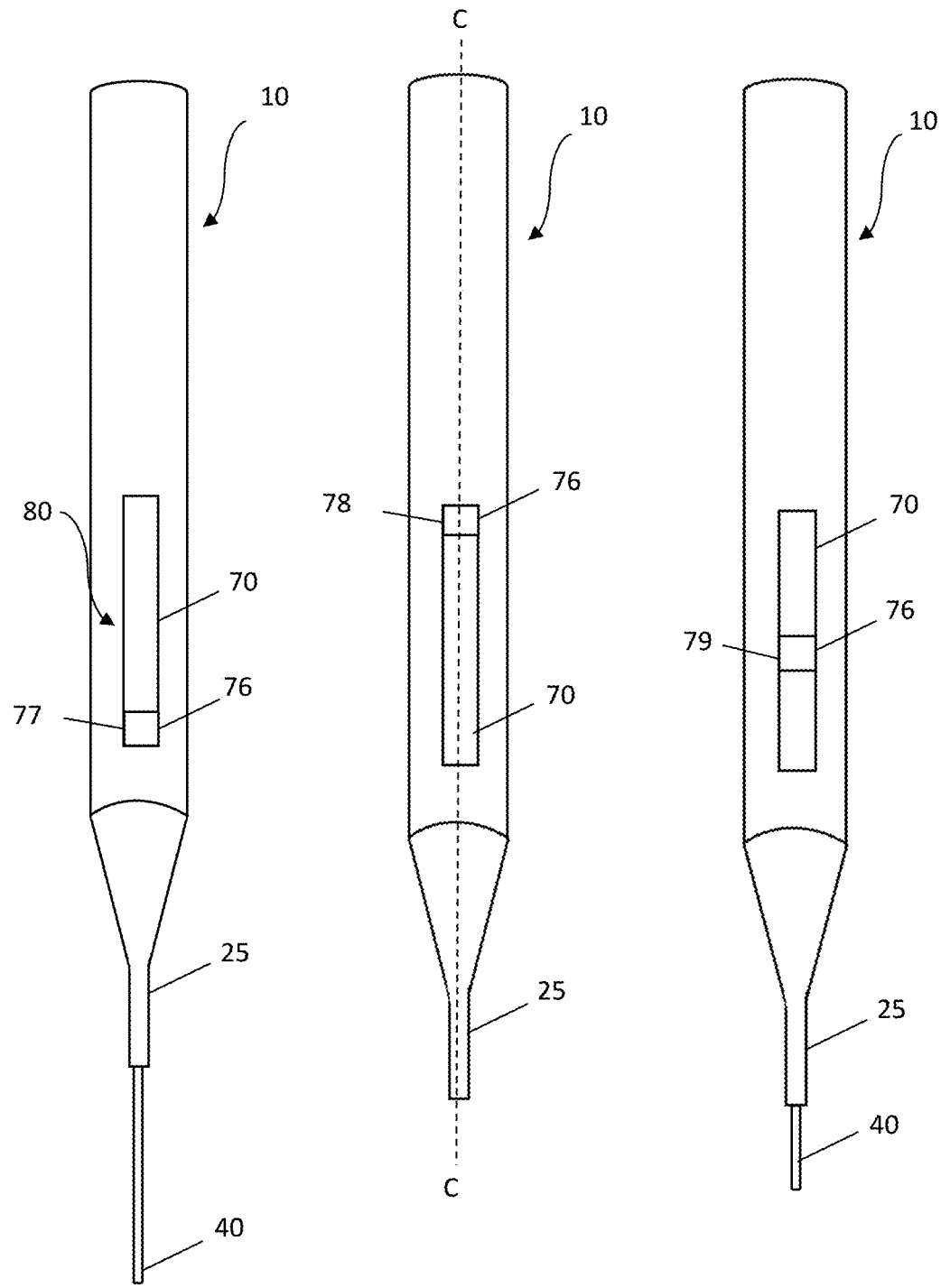
FIG. 10A is a plan view of a second embodiment of the invention including a linear slot for moving and securing the rasp portion in the extending position.
FIG. 10B is a plan view of the embodiment of FIG. 10A with and a linear slot for moving and securing the rasp portion in a retracted position.
FIG. 10C is a plan view of a third embodiment of the invention depicting a linear groove that allows the rasp to extend variable distances.

One benefit of the linear slot system is there may be additional positions of extensions, as shown in FIG. 10C where a position 79 corresponds to a mid-range level of extension between the full retraction 77 and full extension 78. The additional positions may be established by places notches or other securing elements along slot 70.

Locking system 80 is operable methods known in the art of telescoping movement. For example, pushing of button 76 may release a lever from notch 78 and the button may be moved through the slot to position 77 where the button engages another lever and locks the rasp portion 40 in full extension.

Locking system 80 offers the benefit of the central body 30 moving longitudinally without the need to first rotate as with locking mechanism 50. Therefore, if desired, the structures of the central body 30 and outer cover 20 may be altered in various way. For example, FIG. 12. depicts another embodiment of the invention in which the outer cover 20 has one substantially linear or planar surface 74 connected directly to end surface 33 and directly to aperture 21. Planar surface 74 replaces a portion of the annular outer surface 59 of the outer cover 20. Additionally, the central body 30 may be modified to accommodate the planar surface 74. For example, a portion of conical section 24 has been replaced by a substantially planar surface 81. In this embodiment, the bearing surfaces between the abutment portion 34 and abutment cover portion 24 are reduced, and the lower surface of the device is substantially linear or planar rather than annular.

Using the linear slot system 80, also allows the geometric shapes of the handle and abutment portions to incorporate shapes other than conical and cylindrical. For example, the handle cover portion 22 and abutment cover portion 24 may be various shapes including square, rectangular and/or oval, etc. The central body 30 abutment portion 34 and handle portion 32 may also incorporate various including square, rectangular and oval, as desired to properly work with the shape of the outer cover 20.

Figure 13:
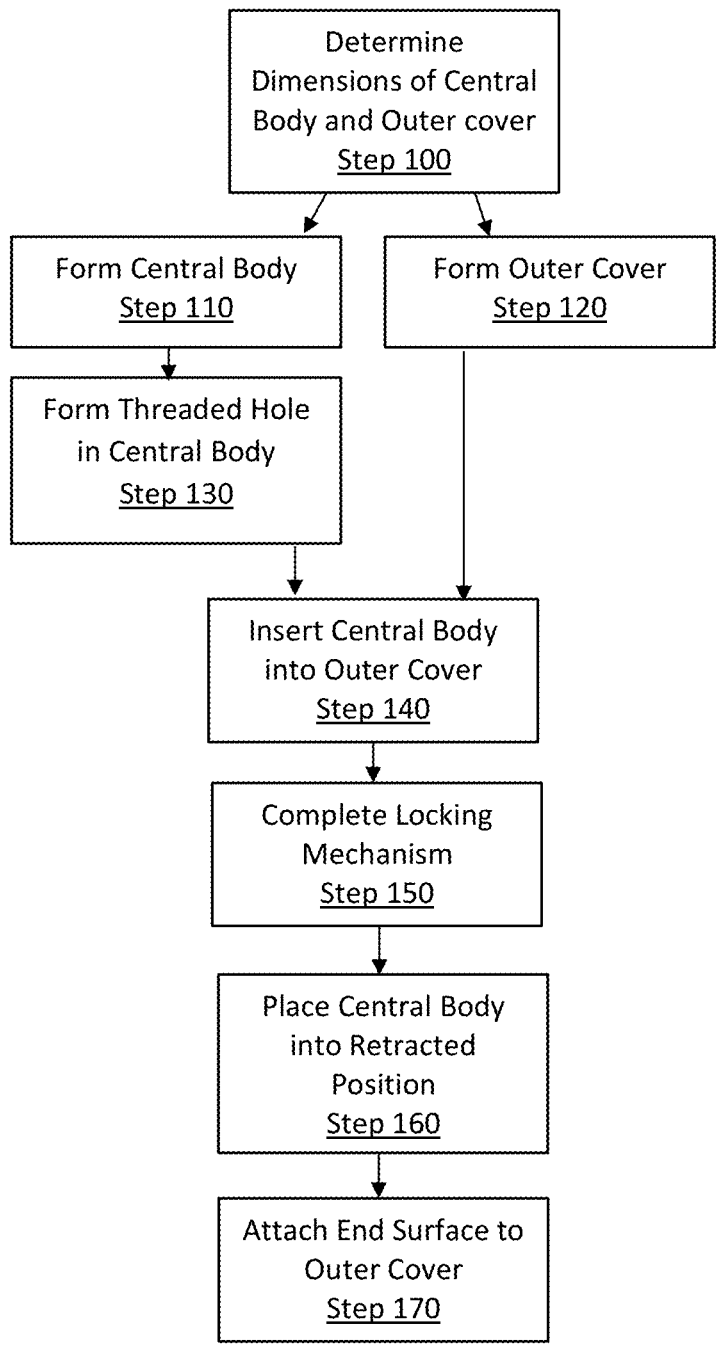
FIG. 13 depicts a preferred embodiment of a method of manufacturing the surgical rasp tool according to this invention.

The preferred embodiment of the surgical rasp tool 10, according to this invention, may be manufactured according to the method depicted in FIG. 13. In the first step 100, the appropriate dimensions of the rasp portion 40, outer cover 20 and central body 30 are ascertained. The rasp portion 40 should be of sufficient length to extend through a prior needle percutaneous access site, skin opening, mucosal opening, surgical opening, and/or body cavity to reach the bone area to be contoured. With respect to rhinoplasty, for example, the rasp portion 40 should be as long as necessary to reach nasal bone formations from the access site through the skin at the lateral nasal sidewall or nasal dorsum inferior and/or anterior to the nasal bones. Additionally, it is desirable for the outer cover 20 to be configured with an appropriate size for proper use by human hands. Based on these two parameters and the discussion above with respect to the dimensions and abutment requirements of the outer cover and central body, the overall dimensions of the surgical rasp tool 10 may be determined.

An example, according to this disclosure, of dimensions for the central body 20 of a surgical rasp tool 10 applicable to rhinoplasty includes the following. The rasp portion 40 may be formed with a length of approximately 3.5 cm, width of 0.14 cm and a height (i.e., distance between the smooth and rough surfaces) of approximately 0.1 cm. The rough surface may be approximately 1.5 cm on one side of the rasp portion 40. The rasp cover portion 25 may have a length of 2 cm and a diameter of 0.16 cm. The handle portion may be approximately 8 cm long and 0.9 cm in diameter.

It is envisioned that the dimensions may change depending on the designated use of the rasp tool 10 and the holder of the tool 10.

In step 110, the central body 30 is provided according to the dimensions determined of step 100. Also, the central body 30 may be formed by the materials and methods described above. Preferably, the central body 30 is formed of a metallic compound such as surgical steel and casting and molding techniques are utilized.

In step 120, the outer cover 20 is formed, according to the dimensions determined in step 100 and may be formed by the materials and methods described above. Preferably, the outer cover 20 is also formed of a metallic compound such as surgical steel and casting and molding techniques are utilized. To allow the central body to be inserted into the outer cover, the closed end surface 43 is not formed in this step. Rather, the appropriate size end surface 43 is formed and saved to be placed on the end, as described below. The end surface 43 may be formed by cutting, milling, stamping or molding a suitable material such as a metallic, plastic and/or ceramic compound.

Additionally, in step 120, the slots 23 or 70 are formed in the wall 5 of the outer cover 20. The desired slot 23 or 70 may be formed in the outer cover 20 by processes such as etching, milling, molding/casting and machining.

Next, in step 130, the hole 27 is formed in the central body 30 for the locking mechanism 50. The hole 27 is formed in the side of the outer surface 32 of the handle portion 31. The hole 27 is oriented such that it extends in a direction transverse to the longitudinally extending central body 30. Also, the hole 27 is placed a position on the central body 30 that will correspond to the slot 23 or 70 when the central body 30 is placed inside the cover 30. Preferably, the hole 27 is threaded, but depending on the corresponding pin or fastener, other hole configurations may be used.

In step 140, the central body 30 is inserted into the outer cover 20. The rasp portion 40 is inserted into the, now, open end 43, and the hole 27 in the central body 30 is aligned with the slot 23, 70 in outer cover 20.

Next, in step 150, the locking mechanism is completed. A threaded annular pin 26 may be selected such that it has a diameter permitting the pin 26 to slide through slot 23, 70. Also, the threaded annular pin 26 should be selected such that it corresponds to the hole 27. The pin 26 is rotationally advanced into hole 27 such that a portion of pin 26 extends from the central body 30 into and/or through the slot 23.

Next, in step 170, the end surface 43 that was formed in step 120 is now attached to the end 43 of the outer cover 20, which was left open in step 120.

The method of attaching may vary based on the material components of outer cover 20. For example, if the outer cover 20 is metal, end surface 43 may be welded onto the opening on the end of the outer cover 20. Other suitable methods are known in the art for attaching materials such as plastics.

The surgical rasp tool 10 may be used to contour areas of bone remote from an incision in the skin. In particular, the surgical rasp tool 10 is intended for, but not limited to, rhinoplasty. Other forms of surgery, such as orthopedic surgery, in humans and animals are contemplated. Additionally, the bone rasp 10 may also be used for other areas where rasps or files are used such as carpentry, pottery and nail manicuring.

Figure 14:
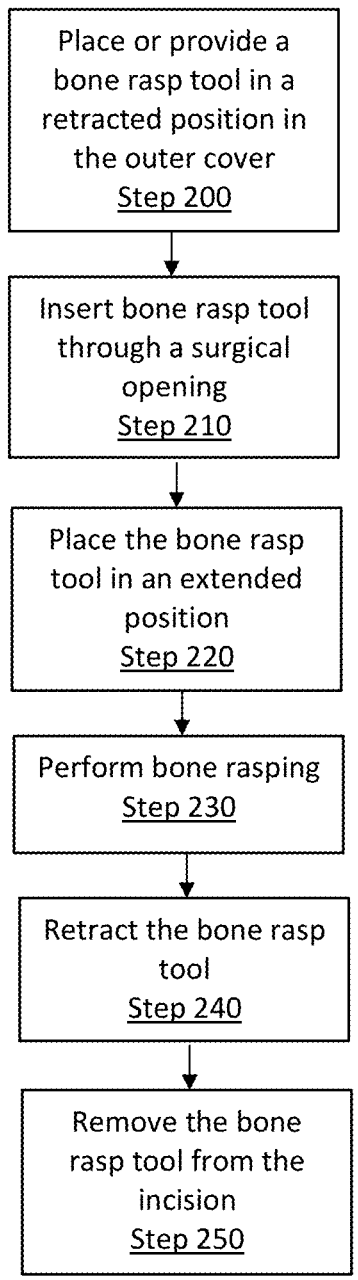
FIG. 14 depicts a preferred embodiment of a method of using the surgical rasp tool of this invention.

FIG. 14 depicts the use of the preferred embodiment of the invention as applied in rhinoplasty. First, in step 200, provide or place the bone rasp tool 10 in the retracted position with the rough surface 35 retracted entirely within the rasp cover portion 25 of outer cover 20.

Next, in step 210, the rasp cover portion 25 is advanced through a surgical opening and under the skin and/or other tissues to an area near a bone formation to be contoured. In rhinoplasty, the incision is generally location adjacent, rather than directly over the bone formation, to be contoured. Therefore, rasp cover portion 25 is advanced to a point adjacent, rather than directly over, the bone formation to be contoured.

Next, in step 220, the bone rasp tool 10 is placed in an extended position so the rough surface 35 of the rasp portion 40 is over and/or close enough to the bone formation to be contoured. This may be accomplished by holding the outer cover 20 in one hand and using a second hand to operate the locking mechanism 50, 80, as described above.

Now, in step 230, bone rasping may ensue with the rough surface being moved across the bone formation to be removed. As is known in the art, this is typically performed with bi-manual pressure. In other words, one hand is holding and moving the rasp tool 10 over the bone and a second hand is placing external, downward pressure over the rough surface. For example, the second hand is pressing on the smooth surface of the rasp 39 through the skin over the bone formation being contoured.

After contouring is complete or has ceased, the rasp portion 40 is retracted, in step 240, into the rasp cover portion 25 of the outer cover 20. This is done by holding the outer cover 20 in one hand and reversing the movement locking mechanism 50, 80, as performed in step 210.

Once fully retracted, in step 250, bone rasp tool 10 is removed from the body through the incision or access site in the skin.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as generally defined in the appended claims.

The invention claimed is:

1. A surgical rasp device comprising:
    a tubular body having an interior surface defining a central opening extending between a first body end and a second body end, the first body end defining a first aperture, the tubular body including:
        a tubular rasp cover portion at the first body end, the tubular rasp cover portion including the first aperture at one end and the tubular rasp cover portion extending in a longitudinal direction;
        a tubular abutment cover portion connected to the tubular rasp cover portion, the tubular abutment cover portion directly connected to a second end of the tubular rasp cover portion, and the tubular abutment cover portion extending a transverse direction relative to the tubular rasp cover portion; and
        a handle cover portion connected directly to the tubular abutment cover portion, and the handle cover portion extending in the longitudinal direction from the tubular abutment cover portion toward the second body end,
        wherein the central opening extends through the tubular rasp cover portion, abutment cover portion and the handle cover portion; and
    a rasp portion connected to the tubular body and positioned in the central opening of the tubular body, the rasp portion including a first side with a rough surface configured to contour bone, and the rasp portion moveable, relative to the tubular body, within the central opening,
    wherein the rasp portion includes a first position with the rough surface contained within the central opening, and a second position with the rasp portion extending through the first aperture such that the rough surface is positioned external to the tubular body, and the rasp portion is moveable from the first position to the second position.

2. The surgical rasp device of claim 1, wherein the rasp portion further comprises:
    a substantially smooth surface opposite and parallel to the rough surface.

3. The surgical rasp device of claim 1, further comprising:
    a first locking mechanism on the tubular body; and
    a second locking mechanism connected to the rasp portion and interlocking with the first locking mechanism,
    wherein the first and second locking mechanisms connect the tubular body to the rasp portion and allow the rasp portion to move relative to the tubular body from the first position to the second position.

4. The surgical rasp device of claim 1, further comprising:
    a central body connected to the rasp portion, the central body positioned in the central opening and within the tubular body, the central body including an outer surface extending around a perimeter of the central body and the outer surface facing the interior surface of the tubular body; and
    a pin connected to the central body, the pin extending from the outer surface of the central body towards the tubular body.

5. The surgical rasp device of claim 4, wherein the tubular body further comprises:
    a slot extending through an outer surface of the tubular body, and the pin extends from the central body through the slot.

6. The surgical rasp device of claim 5, wherein the slot further comprises:
    a first slot end configured to hold the pin when the rasp portion is in the first position; and
    a second slot end configured to hold the pin when the rasp portion is in the second position.

7. The surgical rasp device of claim 5, wherein the tubular body includes a centerline extending in a longitudinal direction, and the slot extends in the longitudinal direction with respect to the centerline.

8. The surgical rasp device of claim 6, wherein the tubular body includes a centerline extending in a longitudinal direction, and the slot further comprises:
    a first segment extending in the longitudinal direction; and
    a second segment extending substantially transverse to the centerline.

9. The surgical rasp device of claim 1, further comprising:
    a central body extending between a first central end and a second central end;
    the rasp portion positioned at the first central end, the rasp portion extending in a longitudinal direction from the first central end towards the second central end;
    a central body abutment portion connected directly to the rasp portion, the central body abutment portion extending in a transverse direction relative to the rasp portion; and
    a handle portion directly connected to the central body abutment portion, the handle portion extending in the longitudinal direction from the central body abutment portion to the second body end.

10. The surgical rasp device of claim 9, wherein, in the first position, the tubular abutment cover portion directly contacts the central body abutment portion, and
 in the second position, the tubular abutment cover portion and the central body abutment portion are spaced apart.

11. A surgical rasp device comprising:
 a tubular body including
  an interior surface defining a central opening extending between a first body end and a second body end, the first body end defining a first aperture, and
  a first body section including a first interior surface; and
 a rasp portion connected to the tubular body and positioned in the central opening of the tubular body, the rasp portion including a first side with a rough surface configured to contour bone, and the rasp portion moveable, relative to the tubular body, within the central opening, the rasp portion including
  a central body connected in line with the rasp portion, and wherein the central body is located in the central opening of the tubular body and the central body circumferentially abuts the first interior surface,
 wherein the rasp portion includes a first position with the rough surface contained within the central opening, and a second position with the rasp portion extending through the first aperture such that the rough surface is positioned external to the tubular body, and the rasp portion is moveable from the first position to the second position.

12. A rasp device comprising:
 a tubular body having an interior surface defining a central opening extending between a first body end and a second body end, the first body end defining an aperture;
 a rasp portion connected to the tubular body and positioned in the central opening of the tubular body, the rasp portion having a first side with a rough surface, and the rasp portion moveable, relative to the tubular body, within the central opening;
 a central body extending between a first central end and a second central end;
 the rasp portion positioned at the first central end, the rasp portion extending in a longitudinal direction from the first central end towards the second central end;
 a central body abutment portion connected directly to the rasp portion, the central body abutment portion extending in a transverse direction relative to the rasp portion; and
 a handle portion directly connected to the central body abutment portion, the handle portion extending in the longitudinal direction from the central body abutment portion to the second body end,
 wherein the rasp portion has a first position with at least the rough surface contained within the central opening, and a second position with the rasp portion extending through the aperture such that the rough surface is positioned external to the tubular body, and the rasp portion is moveable from the first position to the second position.

13. The rasp device of claim 12, wherein the rasp portion further comprises a second side opposite and parallel to the first side, the second side including a substantially smooth surface opposite and parallel to the rough surface.

14. The rasp device of claim 12, further comprising:
 a first locking mechanism on the tubular body; and
 a second locking mechanism connected to the rasp portion and interlocking with the first locking mechanism,
 wherein the first and second locking mechanisms connect the tubular body to the rasp portion and allow the rasp portion to move relative to the tubular body from the first position to the second position.

15. The rasp device of claim 12, wherein the tubular body further comprises:
 a tubular rasp cover portion at the first body end, the tubular rasp cover portion including the aperture at one end and the tubular rasp cover portion extending in a longitudinal direction;
 a tubular abutment cover portion connected to the tubular rasp cover portion, the tubular abutment cover portion directly connected to a second end of the tubular rasp cover portion, and the tubular abutment cover portion extending in a transverse direction relative to the tubular rasp cover portion; and
 a handle cover portion connected directly to the tubular abutment cover portion, and the handle cover portion extending in the longitudinal direction from the tubular abutment cover portion to the second body end,
 wherein the central opening extends through the tubular rasp cover portion, abutment cover portion and the handle cover portion.

16. The rasp device of claim 12, wherein the tubular body has a first length extending between the first body end and the second body end,
 wherein the rasp portion further comprises:
 a first rasp end adjacent the rough surface;
 a second rasp end entirely within the tubular body; and
 a second length extending between the first rasp end and the second rasp end, the second length being less than the first length.

17. A method of making a rasp device, the method comprising:
 providing a tubular body including
  a sidewall extending in a longitudinal direction between a first body end and a second body end,
  a first length between the first and second body ends,
  an interior surface on the sidewall defining a central opening, the interior surface and the central opening extending between the first body end and the second body end,
  a slot extending through the sidewall, the slot extending relatively further in the longitudinal direction than a transverse direction, and
  an aperture at the first body end, and an opening at the second body end;
 providing a central body extending in the longitudinal direction between the first body end, the second body end, the central body including
  a second length extending between the first body end and the second body end, the second length being less than the first length,
  a rasp portion formed at the first body end, the rasp portion including a first side opposite and parallel to a second side, the first side including a rough surface and the second side being entirely smooth, and
  a handle portion connected to the rasp portion and the handle portion extending longitudinally between the rasp portion and the second body end;
 placing a hole in the handle portion of the central body, the hole positioned on the handle portion such that the hole is located within the slot when central body is inserted in the tubular body;
 inserting the central body into the opening in the second body end of tubular body until the central body is contained within the tubular body and the hole is positioned within the slot; and inserting a pin into the hole in the handle portion of the central body.

18. The method of claim 17, wherein providing the central body further comprises:

providing a central body abutment portion between the rasp portion and the handle portion, the central body abutment portion directly connected to the rasp portion and directly connected to the handle portion, and the central body abutment portion extending in a transverse direction.

19. The method of claim 17, wherein providing the tubular body further comprises:

providing a tubular rasp cover portion at the first body end, the tubular rasp cover portion including the aperture at one end;

providing a tubular abutment cover portion connected to the tubular rasp cover portion, the tubular abutment cover portion directly connected to a second end of the tubular rasp cover portion; and providing a handle cover portion connected directly to the tubular abutment cover portion, the handle cover portion extending longitudinally from the tubular abutment cover portion to the second body end, wherein the central opening extends through the tubular rasp cover portion, the tubular abutment cover portion and the handle cover portion.

* * * * *